United States Patent [19]

Sear

[11] Patent Number: 4,798,427

[45] Date of Patent: Jan. 17, 1989

[54] APPARATUS FOR USE IN SUNBATHING

[75] Inventor: John Sear, Coalville, England

[73] Assignee: Sevendart Limited, A Limited Company of U.K., Manchester, United Kingdom

[21] Appl. No.: 872,648

[22] Filed: Jun. 10, 1986

Related U.S. Application Data

[63] Continuation of Ser. No. 640,882, Aug. 15, 1984, abandoned, which is a continuation-in-part of Ser. No. 439,539, Nov. 5, 1982, abandoned.

[30] Foreign Application Priority Data

Mar. 24, 1982 [GB] United Kingdom ............. 8208633

[51] Int. Cl.$^4$ ........................... G02B 5/22; G21F 1/10
[52] U.S. Cl. ................................... 350/1.1; 250/519.1
[58] Field of Search .................... 350/1.1, 1.6, 118; 250/515.1, 519.1

[56] References Cited

U.S. PATENT DOCUMENTS

| | | | |
|---|---|---|---|
| 2,391,959 | 8/1946 | Gallowhur et al. | 350/1.1 |
| 3,298,959 | 1/1967 | Marks et al. | 252/300 |
| 3,382,183 | 5/1968 | Donoian et al. | 252/300 |
| 3,499,914 | 3/1970 | Klink et al. | 260/346.2 |
| 4,167,490 | 9/1979 | Looney | 252/300 |
| 4,200,360 | 7/1980 | Mutzhas | 350/1.6 |
| 4,529,269 | 7/1985 | Mutzhas | 350/312 |

FOREIGN PATENT DOCUMENTS

| | | |
|---|---|---|
| 3101390 | 12/1982 | Fed. Rep. of Germany . |
| 930621 | 4/1946 | France . |
| 2236195 | 10/1973 | France . |
| 2465436 | 3/1981 | France . |
| 1060780 | 9/1967 | United Kingdom . |
| 1540568 | 2/1979 | United Kingdom . |
| 21567979 | 5/1980 | United Kingdom . |
| 1580975 | 12/1980 | United Kingdom . |
| 1586687 | 3/1981 | United Kingdom . |

Primary Examiner—Bruce Y. Arnold
Attorney, Agent, or Firm—Holman & Stern

[57] ABSTRACT

Apparatus for use in sunbathing comprises a screen formed of a sheet of thermoplastic material which is transparent to the safe UV-A wavelengths of solar radiation but which contains uniformly distributed therethrough a first agent whcih absorbs at least 80% of the UV-B radiation in the 290-320 nm range and a second agent which prevents transmission therethrough of some radiations above 450 nm wavelength, i.e. visible light and infra-red. The screen may be mounted on a frame so as to shield the sunbather from the harmful wavelength of radiation, prevent unpleasant overheating and provide subdued lighting. The second agent may be an absorbing dye or pigment.

15 Claims, 5 Drawing Sheets

APPARATUS FOR USE IN SUNBATHING

This is a continuation of application Ser. No. 640,882, filed 8/15/84, now abandoned, which is a continuation-in-part of application Ser. No. 439,539, filed 11/5/82, now abandoned.

BACKGROUND OF THE INVENTION

The current invention relates to a health protecting apparatus for use during sunbathing. It involves the provision of a specially constituted thermoplastic screen offering both shade from the acute and chronic health damaging effects of intense visible and infra-red light, as well as the dangerous invisible short-wave ultra-violet light. At the same time however, the apparatus will permit safe sun-tanning by the transmitted long-wave ultra-violet light. The screen is constituted so as to exclude from the sunbather, by absorption, the major portions of dangerous erythematous and geno-toxic solar radiations, (i.e. short-wave ultra-violet light, UV-B, intense visible white light, and infra red, I.R. wavelengths) at the time of exposure to the natural sun's rays which reach the earth's surface.

Many varied attemps have been made previously to formulate and construct a genuinely safe sun-screen but these have been generally ineffective because at best they only remove the dangerous short wave UV-B either by employing chemical absorbers (e.g. Gallowhur U.S. Pat. No. 2,391,959; Solvay et Cie, French Pat. No. 2236195), by mechanical processing of thermoplastic resins or yarns so as to impart UV-B filtering characteristics (e.g. Solvay et Cie British Pats. Nos. 1540568 and 1580975) or by including ground glass particles in the support resin and providing multiple spatially arranged laminates each with unique but additive absorption characteristics (e.g. Mutzhas British Pats. Nos. 1586687 and 1567979, and U.S. Pat. No. 4,200,360).

However, no previous attempts have been made to remove or reduce all three categories of dangerous light which it now seems (see infra) can interact synergistically to represent a very serious cosmetic and health threatening environment to man.

Recognition of the health hazard of UV-radiation has already prompted the U.S. Department of Health Education and Welfare (via NIOSH) to recommend occupational exposure limits to UV radiation including that of natural sunlight (HSM Pub. No. 73-11009) and there have also been calls by general medical practitioners for stricter controls on UV-parlors (Hawk, 1983; Retsas,1983). Also, a recent U.S. Bureau of Food and Drug Administration advisory panel recommended after reviewing available topical sunscreens: "Over-exposure to the sun may lead to premature ageing of the skin and skin cancer. The liberal and regular use of this product may reduce the chance of premature ageing of the skin and skin cancer".

In addition, apparently successful glass filters have been made and used for, in compliance with for example NIOSH, eye protection from the very dangerous far ultra-violet rays (UV-C) artificially produced by electric carbon arc welding equipment. These glasses employ total UV blockers such as the soluble green dyestuff "Filter-Blaugrun" (British Pat. No. 1060780) and are totally unsuitable for sunbathing because they block the harmless UV-A light as well as eye-sight damaging UV-B and UV-C.

The disadvantages of these earlier screens are that they are either prohibitively expensive to produce, protect the sunbather from only UV-B sunburning rays and not from the overheating or IR-burning rays, or that they block out all the UV-light and prevent tanning altogether. None of the prior art products protect the sunbather from dangerous intense visible or infra-red light which is now thought to be potentially as dangerous as UV-B with respect to cancer induction and skin ageing (see infra).

Terrestrial sunlight has been considered to consist of, with very slight variations of definition, short-wave ultra-violet light (UV-B, 290–320 nm), long-wave ultra-violet light (UV-A: 320–400 nm), visible light (400–700 nm) and infra-red light (wave-lengths ranging from 700–15,000 nm. On a clear day at sea level, the distribution of solar radiation is about 1–2% UV, about 42% visible light and about 57% infra-red. At higher altitudes, at any given latitude, the amount of solar radiation available, especially UV, is increased so much that at the highest altitudes, at sub-zero temperatures a climber needs very effective sunburn protection.

It is now generally recognised that UV-B is dangerous to health and excessive natural exposure can lead to sun-burn (erythema), skin ageing and cancer. UV-A is apparently harmless at natural intensities and induces skin tanning. Visible or white-light has also been considered safe, although there are now reports that there are some disorders of the skin, particularly those involving photosensitivity reactions, skin ageing and cancers, which can occur in those individuals exposed to intense light. The most serious commonly occuring hazards of excessive exposure to visible and infra-red light involve dehydration due to over-heating, ultimately leading to unconsciousness, sunstroke and even death.

Current literature surveys confirm that the deleterious rays of the sun are in the UV region (Cleaver, 1970), and the sun-burning rays (UV-B) are carcinogenic (Blum, 1959, Magnus 1976 and Forbes et al 1978). UV-A on the other hand requires vastly higher exposure doses than UV-B to produce only benign papillomas (Forbes et al 1982).

Sunlight extends of course from the UV-region into the regions of visible light, infra-red and ultimately radio waves. The latter can probably be disregarded with respect to dermal effects, but visible radiation cannot (Kligman & Kligman 1984). Harmful effects such as phototoxic reactions (Kaidby & Kligman 1978) through DNA cross-linking (Gantt et al 1979) to tumor enhancement (Griffin et al 1955) have been recorded. Visible light also causes solar urticaria in some people (Harber & Bichers, 1981).

The precancers and cancers resulting from UV irradiation are now well recognised, but the fact that acute heat exposure can also cause squamous cell carcinomas (Lawrence 1952) is insufficiently well appreciated, as is the fact that chronic heat exposure in the physiological range can result in neoplasm induction. Evidence for these effects are derived from China (Kang cancers), India (Kangri cancers of Kashmir), Japan (Kairo cancer), Ireland (Turf or Peat Fire Cancer), and Australia (epithelioma due to spectacles focussing IR radiation on the cheeks) (See Kligman & Kligman 1984). The similarities between IR and UV induced skin cancers are strikingly obvious (Kligman 1969). In addition, it seems that skin ageing (elastosis and the like), erythema ab igne, and cancers, can be produced by either route and indeed there is a distinct probability that enhancement of chronic actinic damage by IR radiation is of great importance in the etiology of human cancers (Kligman 1982). Clearly, whenever isolation is high, heat is a concomitant factor and sunbathing in the midday sun entails being irradiated by the far from innocuous UV-B and IR rays. The sunscreen formulation described below contains materials arranged so that both heat and UV-B are deflected away from the bather while simultaneously reducing glare by absorption and diffusion of the UV-A and white light.

At present, in order to avoid unpleasant sun-burning and genotoxic effects, premature ageing, solar keratoses, or induced malignant neoplasms, a person who relaxes or is active in strong sunshine is obliged to shield his or her skin from the sun. Such shielding can be effected by the wearing of clothing overall, but this often is not desirable, or even practicable, depending upon the activity being pursued, especially since strong sunshine is usually associated with high temperatures. If the person wishes to be relatively unclothed it is usual to apply creams, lotions or the like to the exposed parts of the body, such substances containing ingredients which purport to absorb some at least of the sun's UV-B, and in some cases UV-A, radiation and thereby prevent or reduce the incidence of the above effects of solarisation. If a person wishes to remain exposed to the sun's radiation for a long period of time, to achieve a suntan for example, frequent and liberal re-application of the cream or lotion is required, which is inconvenient, costly and may itself be a dangerous practice (Lane-Brown et al 1980). Even so, protection from IR either as a direct heating agent or as a cancer inducing agent, or protection from eye-strain, glare, or conjunctivitis, virus activation such as Herpes, dehydration, headache, and the like is of course not provided for by such lotions, and the sunbather is sooner or later obliged to retire from exposure to the sun through heat exhaustion, semi-blindness, and/or by good sense.

As an alternative it may be possible to relax or perform the activity under a roof, canopy or the like which is rendered transparent or translucent to the safe suntanning UV-A radiation but which absorbs the sun's dangerous UV-B and a biologically significant proportion of the sun's visible and IR radiation so as to prevent or reduce the above undesirable effects whilst, at the same time, to permit the desirable effects of shade and tanning.

The beneficial effects of sunlight should not be overlooked. Effects which have been known for many years, e.g. heliotherapy has been used for prophylaxis and treatment of rickets, the synthesis of vitamin D, secondary aneamia, various types of tuberculosis, and skin infections. A deep-seated relation is known to exist between skin tanning and the sex hormone system in males (Hamilton and Herbert 1938) and in females (Hamilton, 1939).

The problem to date has been how to achieve safe and beneficial sunbathing with exclusion of insidious acute and chronic effects.

Most known unpigmented light transparent materials, e.g. glass, quartz, or various types of plastic sheeting, transmit most, if not all, of the sun's dangerous radiation and are, therefore, not suitable for the production of sunscreens since they do not preclude either actinic burning of, dazzle or glare from, heat absorption by, or any chronic synergistic effects in anyone remaining shielded from the sun by such means.

Such materials are used in the construction of so called "sun lamps" and "sun beds". In this case, however, the lamps associated with the equipment are such as to provide only the safe UV-A wavelength range of radiation to produce the tanning effect without burning, and they rely heavily on forced air circulation or heat sinks to provide cooling and heat dissipation. Nevertheless contamination of the emitted UV-A with UV-B is now considered to be a serious deficiency and a potential health hazard to the user of such lamps (Degun et al 1982).

SUMMARY OF THE INVENTION

It is an object of the present invention to provide apparatus for use in sunbathing, of the sunshade type, which is convenient in use and which provides for the transmission of selected wavelengths only of the radiation from the sun.

BRIEF DESCRIPTION OF THE DRAWINGS

Embodiments of the invention are further described with reference to the accompanying drawings in which.

DETAILED DESCRIPTION OF THE INVENTION

The present invention provides apparatus for use in sunbathing in the form of a screen of a plastics material which is transparent to the safe UV-A wavelengths of solar radiation and which contains at least one first agent which absorbs at least 80% of the UV-B radiation and at least one second agent which prevents transmittal of a biologically significant proportion, such biologically significant proportion being above 50% of the visible and IR radiation of wave-lengths in the range 450 to 700 nm and 7000 to 15000 nm respectively through said screen, said agents being uniformly dispersed throughout said plastics material, forming a substantially homogeneous body.

The plastics material, which preferably is a thermoplastic material, must exhibit the property of being transparent to long wave UV-A radiation of wavelengths between 350 and 450 nm which are those particularly associated with tanning. In addition, the wavelengths associated with blinding and a major portion of the IR wavelengths greater than 450 nm are absorbed to exclude the heating element of the sun's radiation, and prevent carcinogenisis and synergistic effects which cause skin ageing or tumor promotion.

Suitable materials for the screen to act as a support material for the first and second agents are resins of vinyl chloride, polyolefins such as polyethylene and polypropylene, or acrylic resins such as polymethylmethacrylate. The vinyl chloride resins referred to are homopolymers or copolymers of vinyl chloride containing more than 50% molar vinyl chloride, and such resins may, in addition contain plasticisers. Copolymers such as polyethylene/vinyl acetate would also suffice, but not thermoplastic materials containing interacting unsaturated or aromatic cores such as polystyrene or polycarbonates which absorb the tanning UV radiation of wavelength greater than 320 nm.

These vinyl chloride or polypropylene type resins are transparent to substantially all of the available UV-A and UV-B wavelengths and most of the visible and IR spectrum.

A preferred material for the screen is a plasticised polyvinyl chloride film of thickness between 100 and 500 microns, for example, 150 microns, and this may be a single film or a laminate formed with a reinforcing nylon net to give greater physical strength.

The sheet material may be impregnated with the first and second agents by dipping the sheet material in an alcoholic solution of the substances. Alternatively the screen material may be prepared by mixing the UV-B visible and IR absorbing materials with the polymer prior to extrusion of and calendering the film.

Whichever of the aforementioned resins is used, it should not have a significant absorption, i.e. greater than 20%, of radiation of wavelengths between 320 and 450 nm. The resin and radiation absorbents should also be light-stable and non-volatile at the relatively high temperatures used in extrusion or calendering (i.e. about 150° C.).

Suitable UV-B absorbing agents include a variety of chemical classes but include such PVC compatible agents as 2-phenylbenzotriazone, or 2-3(hydroxyphenyl) benzotriazone. However, other substances which are stable and which absorb the dangerous short-wave UV-B radiation may be suitable. The sheet material may be impregnated so that between 0.01 and 0.5% by weight and preferably between 0.05 and 0.2% of the UV-B absorbing substance is contained in the thermoplastic material so as to provide the capacity to absorb at least 80% of the naturally available dangerous UV-B radiation of wave-lengths between 290 and 320 nm.

In a similar manner, the visible and infra-red rays of the sun are selectively filtered by including in the composition of the screen a substance or substances, e.g. a dye or pigment, present in sufficient quantity so as to absorb a biologically significant proportion of the radiation of wave-lengths above 450 nm (i.e. above 50%). Because visible light is being removed by this process, a color or tint is imparted into the film. While the color itself has no health effects or benefit, the choice of color or colors will reflect the cosmetic appeal of the apparatus. It is, of course, important to select such absorbant substance or substances which are both PVC, or other resin, compatible, stable and above all which do not absorb wave-lengths between 320 and 450 nm, otherwise the tanning radiation as well as the heating, dazzling and carcinogenic IR radiation would be absorbed. Suitable pigments and dyes would include many chemical classes, for example, Brilliant acid green, and Patent Blue V, and may be present as an admixture in the resin in quantities of less than 0.5% by weight of the screen material.

The UV-B absorbing agents and the pigment or dye must be uniformly dispersed throughout the thermoplastic resin material of the screen.

As mentioned above the sheet material may be derived by extruding or calendering the compounded resin and absorbants.

Additional advantage may be gained by finishing the material so that it has a matt surface finish on one surface and a polished or mirror finish on the other. The matt finished surface provides a means by which the material becomes translucent, to provide privacy and to simultaneously diffuse the transmitted UV-A and some visible light to reduce glare or dazzle, and to avoid focusing the light on the sunbather which may otherwise cause some discomfort. If the screen material is oriented so that the polished surface is towards the sunbather, that surface will reflect back to the bather the desirable and beneficial UV-A rays reflected from him or the ground. This has been found by experiment to be particularly efficacious in the case of a screen provided in the form of a concavo-convex parasol.

The apparatus may also comprise a framework adapted to support said sheet material. Such framework may comprise a central support member and a plurality of support rods extending radially from one end of said central support member. Preferably, the support rods are hingedly attached to the central support member whereby the apparatus may be folded for storage and/or transportation purposes.

Alternatively the support rods may be detachably securable to the central support member for such purpose.

Alternatively the framework may comprise a plurality of support rods over which said sheet material may extend so as to define a screened space therebelow. In this case the support rods may be hingedly or detachably secured to each other.

As a further alternative the sheet material may be adapted to be worn by a person so as to shield a part of that person's body, for example in the form of a hat.

Figure 1:
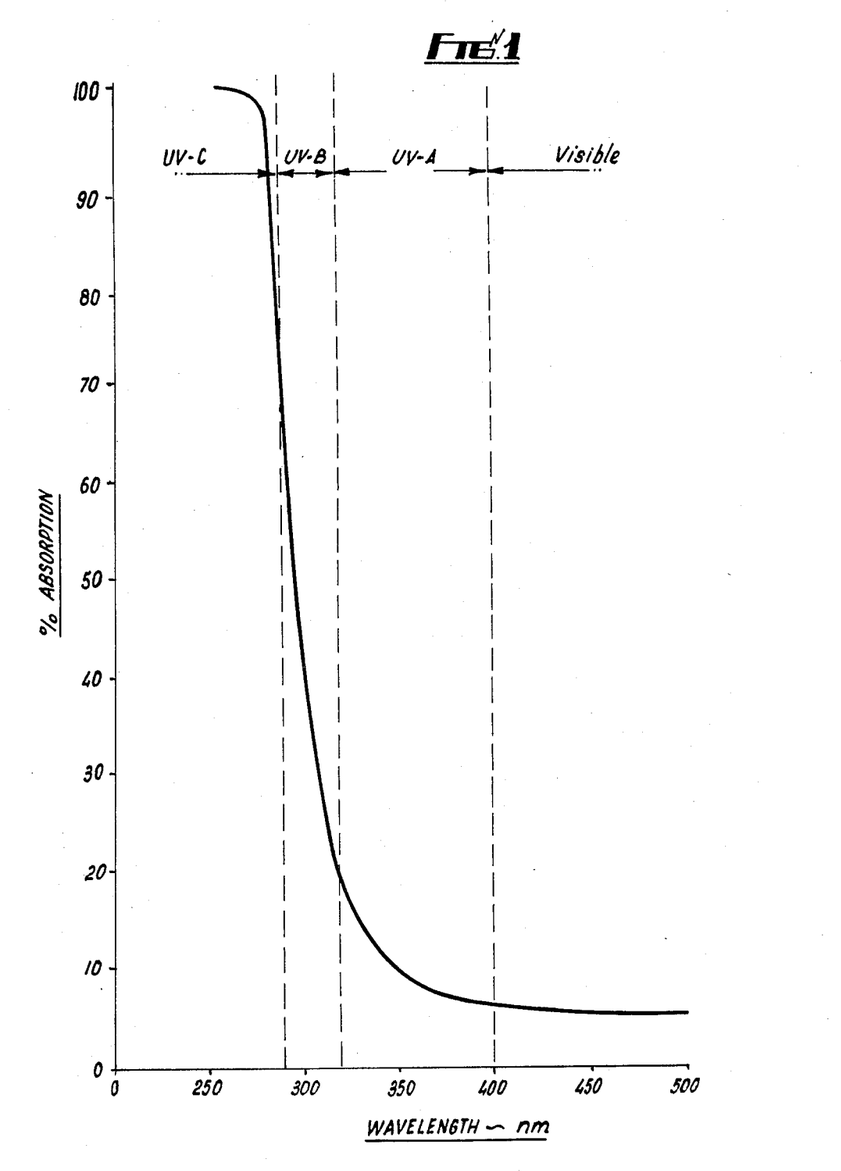
FIGS. 1 and 2 illustrate absorption diagrams or spectrographs for typical plasticised PVC and polyethylene films respectively.
Figure 2:
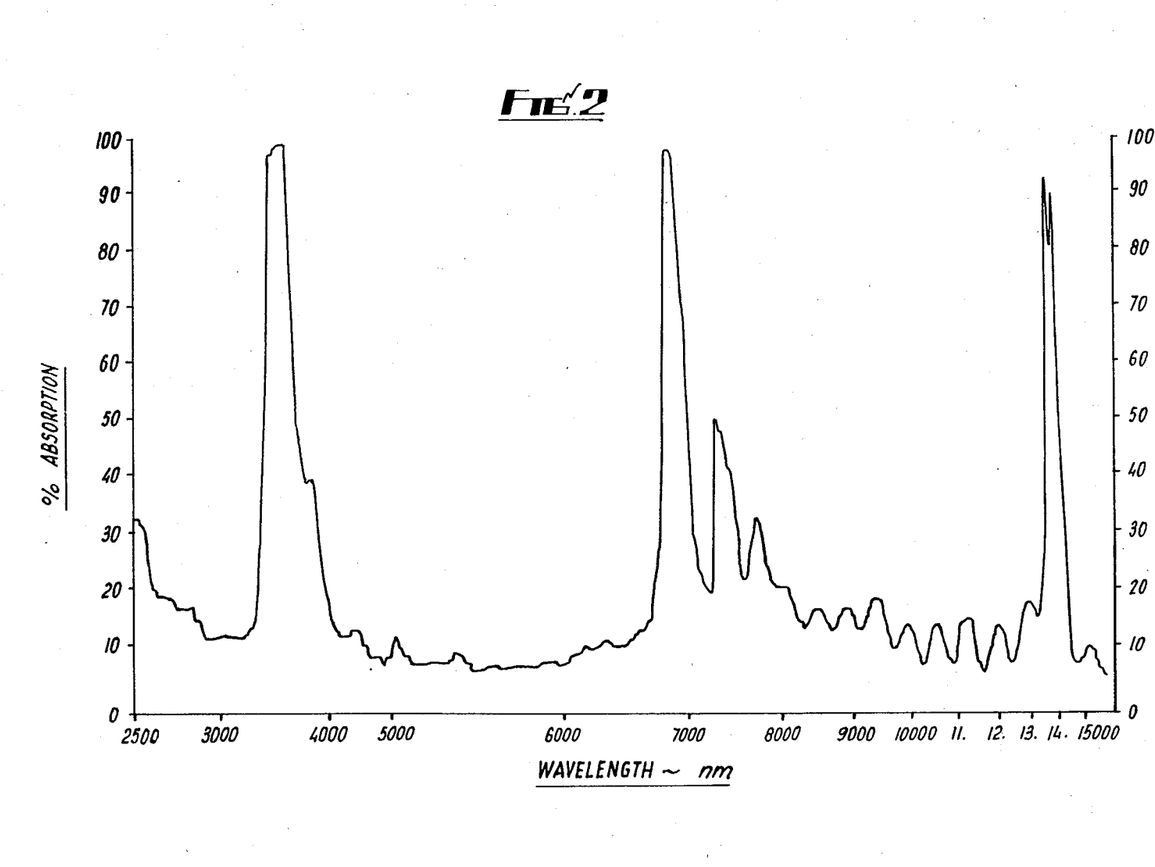

Referring now to FIG. 1 there is shown a spectrograph showing the absorption characteristics of a typical plasticised PVC film. It is to be noted that very little UV-B (i.e. wavelengths between 290 and 320 nm) is absorbed and substantially none of the visible light wavelengths are absorbed. From FIG. 2, which shows an IR spectrograph of a typical plasticised polyethylene film, it can be seen that substantially all of the infra-red wavelengths are transmitted, only three narrow wavelength bands at 3500, 6700 and 14000 nm being absorbed. Neither of these materials would be suitable on their own for the making of an effective sunscreen of the type envisaged by the present invention.

Figure 3:
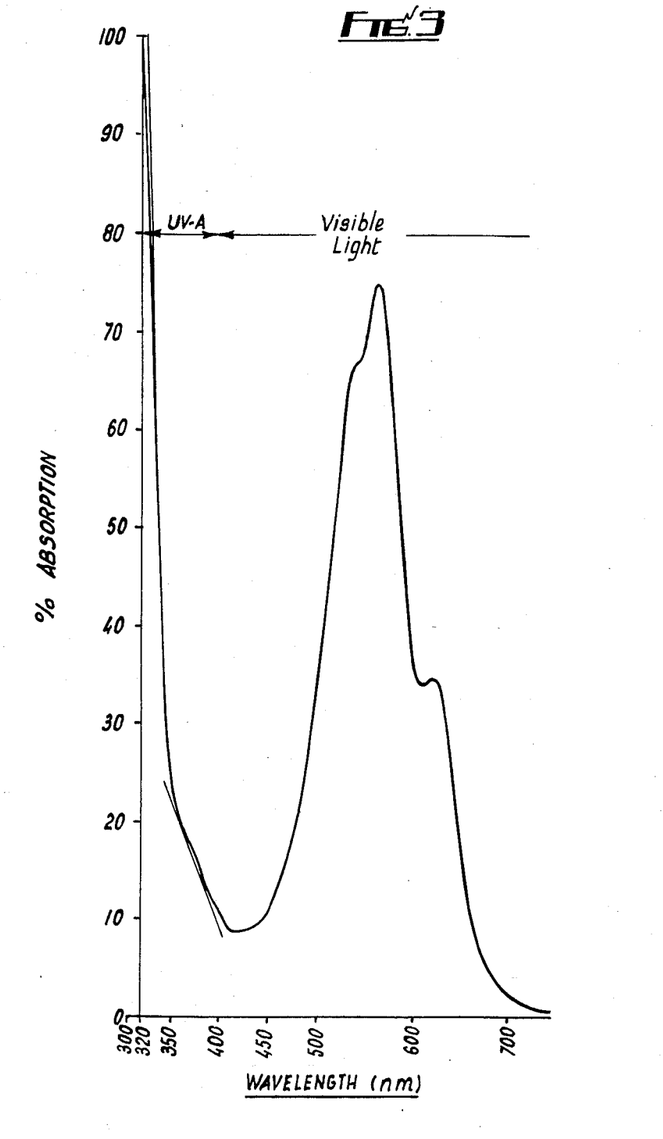
FIG. 3 illustrates a spectrograph of the screen of the invention in the UV and visible light range.
Figure 4:
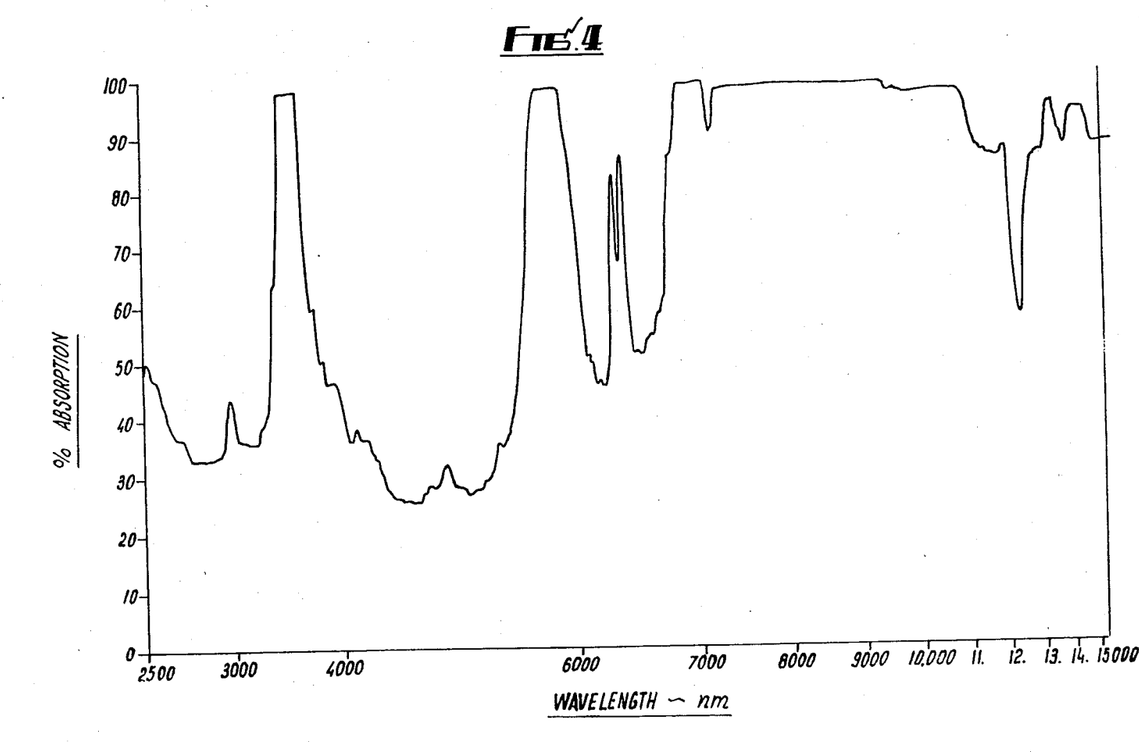
FIG. 4 illustrates a spectrograph of the screen of the invention in the IR range.

Referring now to FIGS. 3 and 4 there are shown absorption diagrams or spectrographs for a screen of the invention. It will be seen that radiation in the UV-B wavelength range 290–320 nm is almost totally absorbed together with a substantial proportion of the radiation in the visible and IR ranges 450 to 700 nm and 2500 to 15000 nm respectively. From FIG. 4 it can be seen that there is almost total absorption of the IR radiation in the wavelength range 7000 to 15000 nm and approximately 50% absorption in the range 2500 to 7000 nm. By this means the harmful radiations of the sun are prevented from reaching a person's skin and eyes. In this way not only is sunbathing or other activity rendered safe from the harmful effects of the sun but such activity may be performed in pleasant subdued and diffused light and without unpleasant heating.

Figure 5:
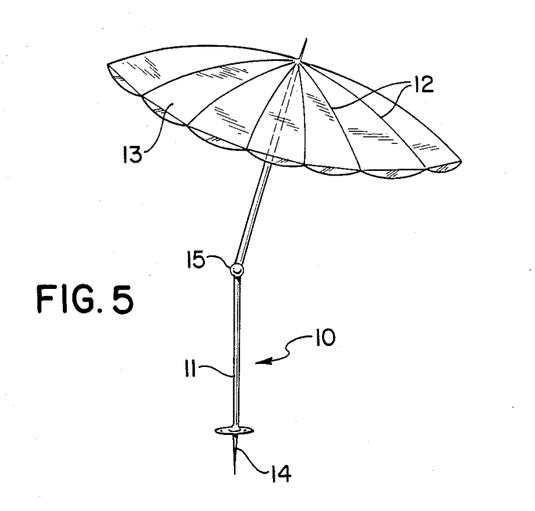
FIG. 5 is a diagrammatic elevation of one embodiment, and, FIG. 6 is a diagrammatic elevation of a second embodiment.

Referring now to FIG. 5 there is illustrated apparatus in the form of an umbrella or parasol 10 of generally conventional construction, which exemplifies a form in which the screen may be supported, and including a central support member 11, a plurality of support rods 12 extending radially from one end of support member 11 and a sheet of material 13 covering and secured to the support rods 12. The umbrella 10 may be folded for storage or transport or erected for use in conventional manner. The central support member 11 is provided with a pointed end 14 to facilitate insertion into, for example, a lawn or beach. Alternatively a heavy disc-shaped base may be provided from which support member 11 is upstanding in use so that the apparatus may be used on impenetrable ground such as a terrace or patio. The support member 11 is hinged at 15 so that the upper part thereof may be directed towards the sun.

Figure 6:
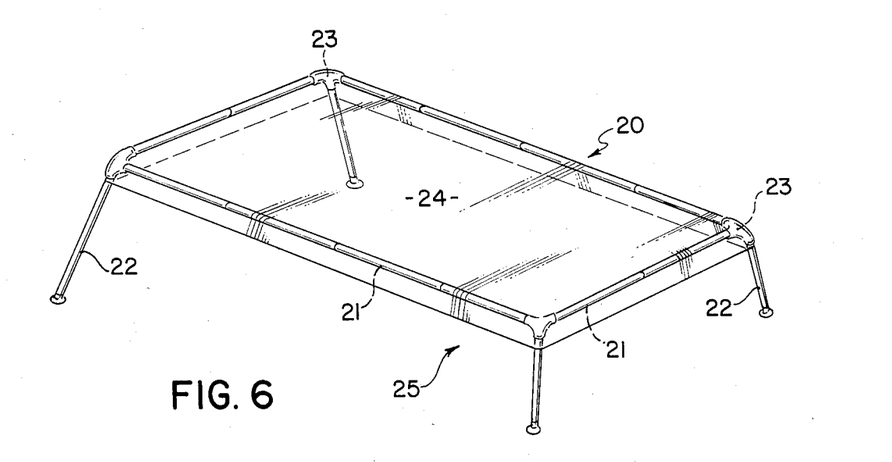

Referring now to FIG. 6 there is shown apparatus in the form of a canopy 20 comprising sheet support rods 21 and legs 22 which are joined together by three-way lugs 23. A sheet of material 24 is supported by rods 21 so as to define a screened space 25 beneath the sheet 24. As shown in the Figure, legs 22 at one end of the apparatus 20 are longer than those at the other end so that the sheet 24 is inclined relative to the ground. Alternatively the legs 22 may be of telescopic construction or comprise interengageable sections which may be assembled in any desired manner so that the sheet 24 may be parallel with the ground or inclined at any desired angle relative thereto. The rods 21 comprise interengageable sections as shown to facilitate transport and/or storage, the length of such sections conveniently being approximately 45 cms so that the plan area of the canopy 20 as shown is approximately 180×80 cms. The rods 21 and legs 22 are removably engageable with legs 23 and may be of plastic material, light alloy or steel.

Alternatively pivotal attachments may be provided if desired. The sheet 24 may be secured to rods 21 by clips, studs or ties (not shown), by being enclosed in pockets (not shown) formed along the edges of the sheet 24, or by any other known method which preferably allows removal of the sheet 24 from the rods 21.

In any one of the many possible embodiments of the apparatus of the invention the sheet material 13, 24 is transparent to the tanning UV-A radiation, but includes substances which absorb at least 80% of the UV-B radiation in the 290 to 320 nm wavelength range, and at least 50% of the visible light and IR wavelengths above 450 nm. By means of the invention a person can be shielded from the deleterious effects of the sun and will develop a suntan while relaxing or being active outdoors without the necessity of either the frequent application of creams, lotions or the like or the wearing of restricting or undesirable clothing.

Atlernative embodiments of apparatus will be readily apparent to persons skilled in the art. For example the screen material may be laminated with nylon net to provide sufficient strength for it to be used for example as a roof for an enclosure such as a swimming pool or tennis court. Also many other configurations of framework may be used in the manner of the embodiment of FIG. 6, for example a simple upright support screen. Alternatively the screen material may be formed in the shape of for example a wide-brimmed hat such as may be worn by a person exposed to the sun.

BIBLIOGRAPHY.

U.S. Dept. HE & W (NIOSH) HSM Publication No. 73-11009.
Hawk JLM (1983) Brit. Medical Journal 286 329.
Retsas S. (1983) Brit. Medical Journal 286 892.
Cleaver J. (1970) J. Invest. Dermatology 54 181.
Blum HF (1959) Carcinogenesis by ultraviolet light p 185 Princetown Univ. Press., Princetown, N.J.
Magnus IA (1976) Dermatologic Photobiology p. 177 Blackwell, London.
Forbes PD et al (1978) Nat. Cancer Inst. Monograph 50 131
Forbes PD et al (1982) Photocarcinogenesis by UV-A alone. Abstracts p 66. Ann. Meeting, Am. Soc. Photobiol. Vancouver BC Canada.
Kligman LH & Kligman AM (1984). Brit. J. Dermatology 110 369.
Kaidbey KH & Kligman AM (1978). Journal Invest. Dermatol. 70 149.
Gantt R et al (1979) Biochimica et Biophysica Acta 565 231.
Griffin AC et al (1955) Cancer Research 10 523.
Harber LC & Bickers DR (1981) Photosensitivity Diseases p 160. W. B. Saunders, Philad.
Lawrence EA (1952) Surgery, Gynecology & Obstetrics 95 579.
Kligman AM (1969) J. American, Med. Association 210 2377.
Kligman LH (1982) Archives of Dermatology Research 272 229.
Lane-Brown MM et al (1980) Med. Journal. Australia 1 283.
Hamilton & Herbert (1938) Science 88 481.
Hamilton (1939) Proc. Soc. Experimental. Biol. Med. 40 502.
Devgun MS et al (1982). Brit. Journal Dermatol 107 275.

I claim:

1. A radiation filter for use in sunbathing comprising: a screen of a plastic material; said plastic material being substantially transparent to the safe UV-A wavelengths of solar radiation and substantially transparent to visible wavelengths of solar radiation; said screen containing at least one first agent which absorbs at least 80% of incident solar UV-B radiation and at least one second agent which prevents transmittal of a biologically significant proportion of above 50% of incident visible solar radiation and incident IR solar radiation of wavelength in the ranges 450 to 700 nm and 7000 to 15000 nm respectively through said screen;

said first agent and said second agent being substantially uniformly dispersed throughout said screen; said screen being transmissive of at least 80% of solar radiation in the UV-A wavelengths, and being transmissive of at least approximately 50% of incident visible and IR solar radiation 2. A radiation filter according to claim 1 wherein said screen is a flexible sheet.

3. A radiation filter according to claim 2, wherein said plastic material is a thermoplastic material.

4. A radiation filter according to claim 3 wherein said thermoplastic material is selected from the group consisting of a resin of vinyl chloride, polyolefin, or an acrylic.

5. A radiation filter according to claim 1 wherein said first agent comprises between 0.01 and 0.5% by weight of said screen.

6. A radiation filter according to claim 1 wherein said second agent comprises less than 0.5% by weight of said screen.

7. A radiation filter according to claim 1 wherein said second agent comprises a light stable and heat stable pigment.

8. A radiation filter according to claim 1 further comprising a framework supporting said screen.

9. A radiation shield for promoting pigmentation of human skin by solar radiation, comprising:

a screen; said screen including a sheet-like, substantially homogeneous body;

said substantially homogeneous body being composed of a plastic composite material;

said plastic composite material being composed of approximately 99% by weight of thermoplastic material;

said plastic composite material including a substantially uniformly dispersed first filtering agent in a range of 0.5% or less by weight of said plastic composite material; said substantially homogeneous body being sufficiently thick that said first filtering agent causes said substantially homogeneous body to absorb approximately at least 80% of incident UV-B solar radiation without absorbing a relatively significant amount of incident UV-A solar radiation;

said plastic composite material including a substantially uniformly dispersed second filtering agent of 0.5% or less by weight of said plastic composite material; said substantially homogeneous body being sufficiently thick that said second filtering agent causes said substantially homogeneous body to absorb at least approximately 50% of incident visible 450 nm–750 nm wavelength solar radiation and at least approximately 50% of incident 7,000 nm–15,000 nm wavelength solar radiation;

said substantially homogeneous body being generally substantially transparent to incident UV-A solar radiation; said substantially homogeneous body transmitting approximately at least 50% of incident visible 450–700 nm solar radiation;

whereby "safe" UV-A radiation is trasmitted to permit tanning, "harmful" UV-B radiation is substantially blocked, and a major portion of the radiation wavelengths associated with "blinding" and heat are blocked.

10. A radiation shield as claimed in claim 9, wherein said thermoplastic material is selected from the group consisting of resins of vinyl chloride, polyolefins such as polyethylene and polypropylene, or other acrylic resins such as polymethyl-methacrylate.

11. A radiation shield as claimed in claim 9, wherein said first filtering agent is 2-phenylbenzotriazone.

12. A radiation shield as claimed in claim 9, wherein said second filtering agent is selected from the group consisting of brilliant acid green or Patent Blue V.

13. A radiation shield as claimed in claim 9, wherein said screen is of plasticized polyvinyl chloride; said screen having a thickness in a range of 100 microns to 150 microns.

14. A radiation shield as claimed in claim 13, further comprising a reinforcing sheet for reinforcing said screen.

15. A radiation shield as claimed in claim 9, wherein said screen further comprises a plasticizing agent.

* * * * *